(12) United States Patent
Valentin et al.

(10) Patent No.: US 7,128,733 B2
(45) Date of Patent: Oct. 31, 2006

(54) INCONTINENCE ARTICLE HAVING A BACK GUARD

(76) Inventors: Tara J. Valentin, 1980 Western Ave., Apt. 932, Albany, NY (US) 12203; Stacey A. Infantino, P.O. Box 132, South Cairo, NY (US) 12482-0132

( * ) Notice: Subject to any disclaimer, the term of this patent is extended or adjusted under 35 U.S.C. 154(b) by 0 days.

(21) Appl. No.: 09/871,717

(22) Filed: Jun. 1, 2001

(65) Prior Publication Data
US 2002/0183706 A1    Dec. 5, 2002

(51) Int. Cl.
*A61F 13/15* (2006.01)
(52) U.S. Cl. ............ 604/385.16; 604/385.01; 604/385.11; 604/385.3; 604/385.25; 604/385.23
(58) Field of Classification Search ......... 604/385.01, 604/385.11, 385.3, 385.25, 385.23, 385.16; 2/400–407, 238, 227, 69, 78.1, 92, 267, 455, 2/467
See application file for complete search history.

(56) References Cited

U.S. PATENT DOCUMENTS

| | | | |
|---|---|---|---|
| 620,435 A * | 2/1899 | Fisher | 2/227 |
| 1,771,253 A * | 7/1930 | Goldstein | 2/102 |
| 1,998,140 A | 4/1935 | Loew | |
| 2,630,120 A | 3/1953 | Nielson | |
| 4,072,150 A * | 2/1978 | Glassman | 604/389 |
| 4,265,245 A * | 5/1981 | Glassman | 604/365 |
| 4,578,072 A | 3/1986 | Lancaster | |
| 4,738,677 A | 4/1988 | Foreman | |
| 4,938,753 A | 7/1990 | Van Gompel et al. | |
| 5,026,364 A * | 6/1991 | Robertson | 604/385.3 |
| 5,105,473 A * | 4/1992 | Valtakari | 2/461 |
| 5,106,385 A | 4/1992 | Allen et al. | |
| D330,080 S | 10/1992 | Norberg | |
| H1440 H | 5/1995 | New et al. | |
| 5,514,121 A * | 5/1996 | Roe et al. | 604/385.19 |
| 5,520,674 A * | 5/1996 | Lavon et al. | 604/385.16 |
| 5,531,730 A | 7/1996 | Dreier | |
| 5,558,659 A | 9/1996 | Sherrod et al. | |
| 5,558,660 A | 9/1996 | Dreier | |
| 5,601,545 A * | 2/1997 | Glaug et al. | 604/385.29 |
| 5,758,367 A * | 6/1998 | Torrent Lopez et al. | 2/400 |
| 5,795,347 A | 8/1998 | Roe et al. | |
| 5,833,677 A * | 11/1998 | Sauer | 604/369 |
| 5,858,012 A | 1/1999 | Yamaki et al. | |
| 5,938,652 A * | 8/1999 | Sauer | 604/385.29 |
| 5,989,236 A | 11/1999 | Roe et al. | |
| 6,119,275 A * | 9/2000 | Goyal | 2/400 |
| 6,132,410 A * | 10/2000 | Van Gompel et al. | 604/385.25 |
| 6,258,076 B1 * | 7/2001 | Glaug et al. | 604/387 |
| 6,264,639 B1 * | 7/2001 | Sauer | 604/385.101 |
| 6,280,426 B1 | 8/2001 | Turner et al. | |
| 6,317,893 B1 * | 11/2001 | Walton | 2/227 |
| 6,425,889 B1 * | 7/2002 | Kitaoka et al. | 604/385.01 |
| 6,450,997 B1 | 9/2002 | Seitz et al. | |
| 6,482,196 B1 * | 11/2002 | Hisada | 604/385.3 |
| 6,506,185 B1 | 1/2003 | Sauer et al. | |

* cited by examiner

*Primary Examiner*—Jacqueline F. Stephens
(74) *Attorney, Agent, or Firm*—Hoffman, Warnick & D'Alessandro

(57) ABSTRACT

An incontinence article having a back guard is provided. In particular, the present invention provides an incontinence article in which a back guard extends from a rear portion of the article to a middle back area of a user. The back guard article preferably includes an absorbent material and optional elastic.

28 Claims, 14 Drawing Sheets

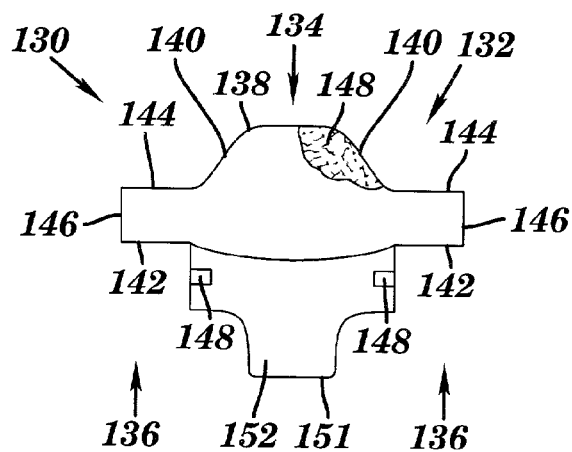
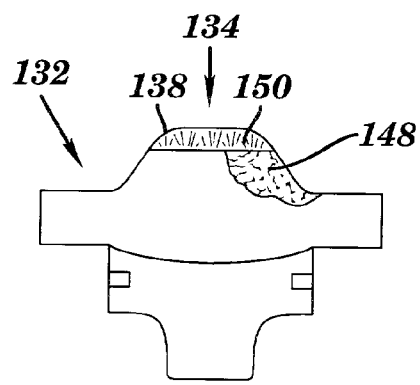
FIG. 6A
FIG. 6B
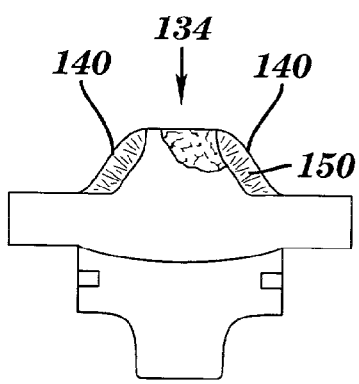
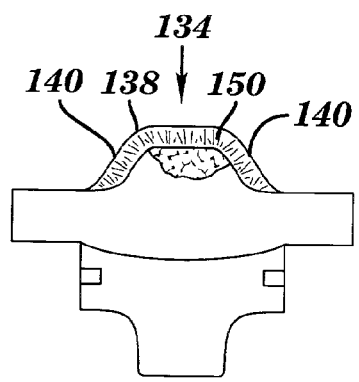
FIG. 6C
FIG. 6D
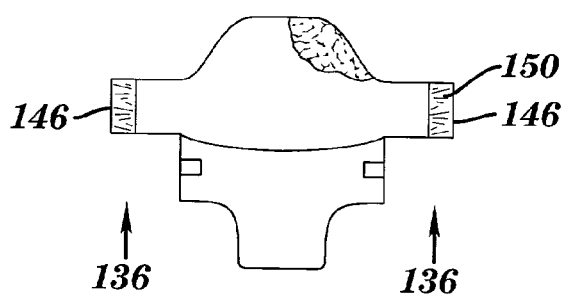
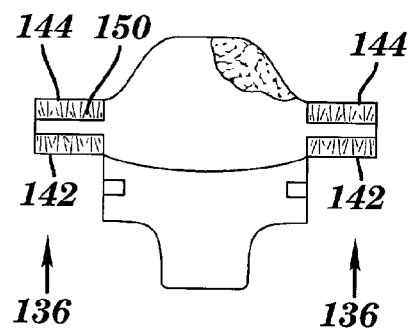
FIG. 6E
FIG. 6F

INCONTINENCE ARTICLE HAVING A BACK GUARD

BACKGROUND OF THE INVENTION

1. Technical Field

The present invention generally relates to an incontinence article having a back guard for protecting the back and clothing of a user. More particular, the present invention relates to an incontinence article for children or adults in which a back guard extends from a rear portion of the article to the middle back torso area of the user.

2. Background Art

The use of disposable incontinence articles is gaining widespread use in the care of both children and adults. A typical incontinence article (e.g., a diaper) is a multilayered composite structure that includes a liquid permeable body-side layer, a liquid impermeable outer cover, and an absorbent material positioned between the outer cover and the body-side liner.

Children's diapers are generally flat garments intended to be fit around a child while lying down. Adult incontinence articles are usually constructed with multiple layers similar to a child's diaper, but are often made thinner and narrower for improved discreteness. Moreover, many adult incontinence articles are constructed to be slipped on by a user similar to a pair of shorts However, a problem unrecognized by existing incontinence articles is that, when worn, waste products often leak to the back torso area of the user. This is generally caused, for example, when the user shifts between a seated position and a standing position, or between a seated position and a lying position. In addition, due to new guidelines set forth by the Sudden Infant Death Syndrome (SIDS) Alliance and the American Academy of Pediatrics, children are increasingly being placed on their backs' to sleep, which causes leakage. When waste products leak, the user's back often becomes soiled and his/her clothing becomes ruined.

Heretofore, attempts have been made to reduce leaking in incontinence articles by improving the absorbent material and/or improving the fit of the article to the user (e.g., by providing additional or improved elastic systems). However, none of these systems truly prevent waste from leaking to the back of the user. One such example is shown in U.S. Pat. No. 5,858,012 to Yamaki et al., herein incorporated by reference. Yamaki et al. provide a short band of elastic extending from a rear portion of a diaper. However, due to the lack of absorbent material around the band of elastic, as well as the short length thereof, the user's back and clothes are still at risk.

In view of the forgoing, there exists a need for an incontinence article having back guard that extends from a rear portion of the article to the middle back area of the user. This prevents leakage of waste products from the article to the back of the user.

SUMMARY OF THE INVENTION

The present invention overcomes the problems of existing devices by providing an incontinence article having a front portion, a rear portion, and a back guard extending from the rear portion to a middle back area of a user. The back guard can include an absorbent material as well as optional elastic for ensuring a snug fit to the user.

According to a first aspect of the present invention, an incontinence article is provided. The article comprises: (1) a front portion; (2) a rear portion joined to the front portion; and (3) a back guard extending from the rear portion to a middle back area of a user.

According to a second aspect of the present invention, an incontinence article is provided. The article comprises: (1) a front portion; (2) a rear portion joined to the front portion; and (3) a back guard extending from the rear portion, wherein the back guard has a length of approximately 1.0 to 10.0 inches, and wherein the back guard includes an absorbent material.

According to a third aspect of the present invention, an incontinence article is provided. The article comprises: (1) a front portion; (2) a rear portion joined to the front portion; and (3) a back guard extending from the rear portion, wherein the back guard comprises an absorbent material and separately positioned elastic.

According to a fourth aspect of the present invention, an incontinence article is provided. The article comprises: (1) a front portion for contacting a front side of a user; (2) a rear portion for contacting a rear side of the user; (3) a crotch portion joining the front portion to the rear portion; (4) a back guard extending from the rear portion to a middle back area of a user, wherein the back guard has: (a) a length of approximately 1.0 to 10.0 inches; (b) an absorbent material positioned centrally on the back guard; and (c) elastic positioned about a periphery of the back guard.

According to a fifth aspect of the present invention, an incontinence article is provided. The article comprises: (1) a front portion; (2) a rear portion joined to the front portion; and (3) a back guard extending from the rear portion, wherein the back guard comprises a vertical extension and opposing horizontal extensions.

According to a sixth aspect of the present invention, an incontinence article is provided. The article comprises: (1) a front portion; (2) a rear portion joined to the front portion; and (3) a back guard extending from the rear portion to a middle back area of a user, wherein the back guard comprises a vertical extension, opposing horizontal extensions, and an absorbent material.

According to a seventh aspect of the present invention, an incontinence article is provided. The article comprises: (1) a front portion; (2) a rear portion joined to the front portion; and (3) a back guard extending from the rear portion to a middle back area of a user, wherein the back guard comprises a vertical extension having a length of approximately 1.0 to 10.0 inches and opposing horizontal extensions each having a length of approximately 1.0 to 10.0 inches, and wherein the back guard includes an absorbent material and separately positioned elastic.

According to an eighth aspect of the present invention, an incontinence article is provided. The article comprises: (1) a front portion; (2) a front guard extending from the front portion to a middle chest area of a user; (3) a rear portion joined to the front portion; (4) a back guard extending from the rear portion to a middle back area of a user; and (5) wherein the front and rear portions each comprise an absorbent material.

According to a ninth aspect of the present invention, an incontinence article is provided. The article comprises: (1) a front portion; (2) a rear portion joined to the front portion; and (3) a back guard extending from the rear portion, wherein the back guard comprises an absorbent material and elastic.

Therefore, a preferred embodiment of the present invention provides an incontinence article having a back guard. The article includes a front portion, a rear portion joined to the front portion, and a back guard extending from the rear portion to approximately a middle back area of a user.

BRIEF DESCRIPTION OF THE DRAWINGS

These and other features and advantages of this invention will be more readily understood from the following detailed description of the various aspects of the invention taken in conjunction with the accompanying drawings in which:

FIGS. 2A–E depict front views of an incontinence article having a back guard according to a first embodiment of the present invention.

FIGS. 3A–E depict front views of an incontinence article having a back guard according to a second embodiment of the present invention.

Figure 1:
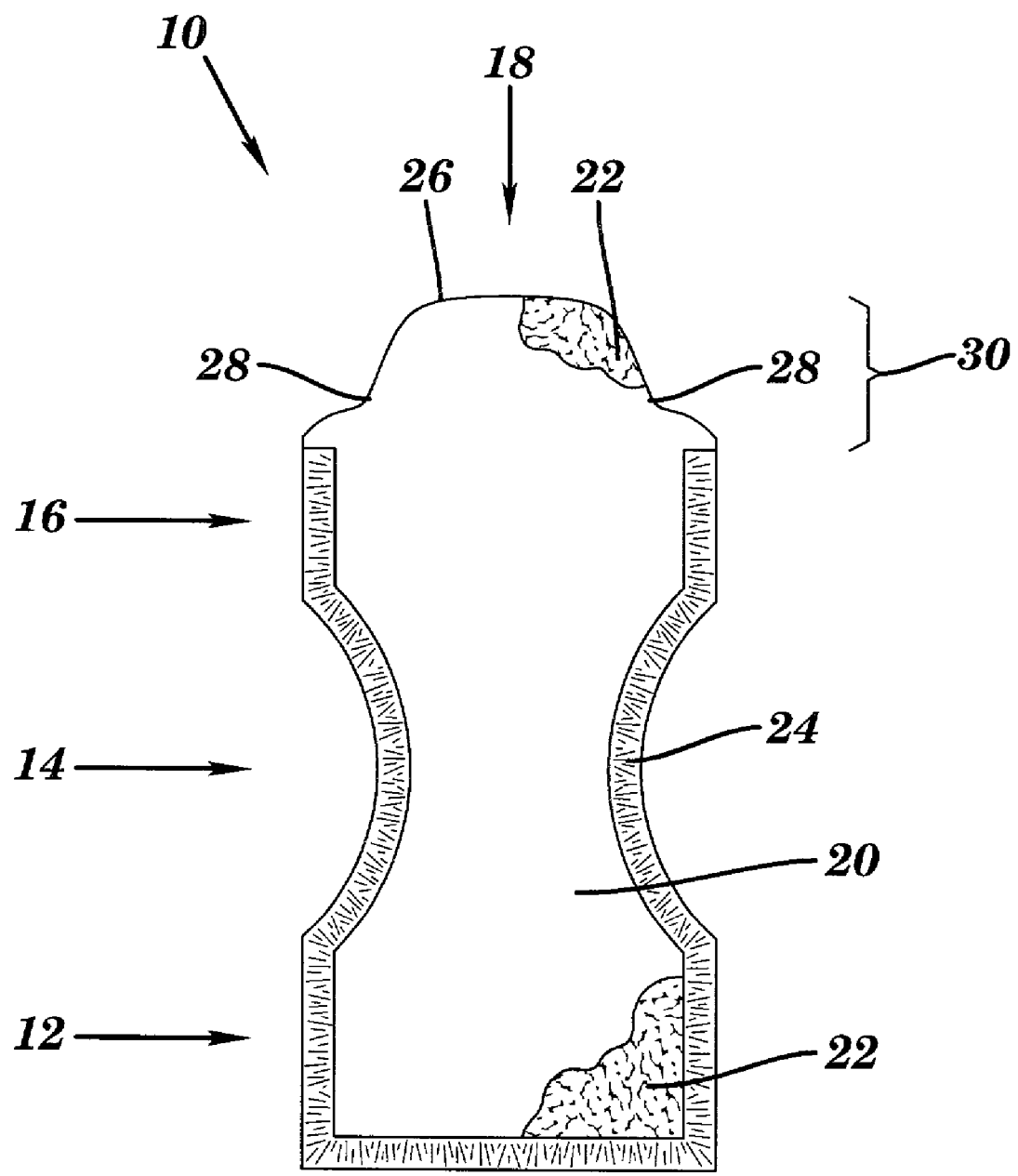
FIG. 1 depicts a plan view of an unfolded incontinence article, according to the present invention.

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE DRAWINGS

Referring now to FIG. 1, an incontinence article 10 according to the present invention is shown. Article 10 is a diaper, or the like, and can be used by children or adults. Article 10 generally includes: front portion 12 for contacting a front side of a user; rear portion 16 for contacting a rear side of a user; crotch portion 14 joining the front portion to the rear portion for contacting a crotch of a user; and back guard 18. As shown, back guard 18 extends from rear portion 16 and can be connected to rear portion 16 as an attachment or can be formed as a continuous body with rear portion 16 (as shown in FIG. 1).

The construction of article 10 is well known in the art. Specifically, article 10 preferably includes three layers: (1) a liquid permeable body-side layer 20; (2) a non-permeable outer cover (not shown in FIG. 1); and an absorbent material 22 between the outer cover and the body-side layer 20. Liquid permeable body-side layer 20 can be any soft, flexible, porous sheet, which allows fluids to pass therethrough. For example, body-side layer 20 could be: (1) a non-woven web or sheet of wet strength tissue paper; (2) a spunbonded, meltblown, or bonded-carded web composed of synthetic polymer filaments, such as polyproplyene, polyethylene, polyesters or the like; or (3) a web or natural polymer filaments such as rayon or cotton. Outer cover is preferably a liquid impermeable material such as, for example, a web or sheet of plastic film. Absorbent material 22 is preferably a material (e.g., wood pulp fluff) capable of absorbing and retaining fluids. These and other possible materials for article 10 are shown and described in U.S. Pat. Nos. 4,938,753 to Van Gompel et al. and 5,558,659 to Sherrod et al., both of which are herein incorporated by reference. However, it should be understood that the materials used to construct the incontinence articles of the present invention are for illustrative purposes only and are not intended to be a limiting feature. Along a periphery of the front portion 12, crotch portion 14, and rear portion 16 is retention system 24. Retention system 24, which is preferably elastic, allows article 10 to be snugly fitted on the user and helps prevent waste products from leaking out of the sides.

Back guard 18 will be described in further detail below, but similar to portions 12, 14, and 16 of article 10, includes a liquid permeably body-side layer, a non-permeable outer cover, and an absorbent material therebetween. Moreover, as indicated above, back guard 18 extends from rear portion 16 to a middle back area of a user. Because the users will vary in size, back guard 18 can be made any length capable of extending to a middle back area of an intended user. Thus, for example, back guard 18 can have any length 30 anywhere from approximately 1.0 to 24.0 inches. Preferably, back guard 18 has a length 30 of approximately at least 1.0 inches, and more preferably, a length 30 of approximately 1.0 to 10.0 inches. In an alternative embodiment, back guard 18 has a length 30 of at least 1.5 inches, and more preferably, a length 30 of approximately 1.5 to 10.0 inches. In an alternative embodiment, back guard 18 preferably has a length 30 of approximately at least 2.0 inches, and more preferably, a length 30 of approximately 2.0 to 10.0 inches. In an alternative embodiment, back guard 18 has a length 30 of at least approximately 3.0 inches, and more preferably, a length 30 of approximately 3.0 to 10.0 inches. In another embodiment back guard 18 has a length 30 of at least approximately 4.0, and more preferably, a length of approximately 4.0 to 10.0 inches. In an alternative embodiment, back guard 18 preferably has a length 30 of approximately at least 5.0 inches, and more preferably, a length 30 of approximately 5.0 to 10.0 inches. In an alternative embodiment, back guard 18 preferably has a length 30 of approximately at least 6.0 inches, and more preferably, a length 30 of approximately 6.0 to 10.0 inches. In an alternative embodiment, back guard 18 preferably has a length 30 of approximately at least 7.0 inches, and more preferably, a length 30 of approximately 7.0 to 10.0 inches. Accordingly, it should be realized that length 30 of back guard 18 can be of any value or range of values between 1.0 and 24.0 inches. These possible lengths and/or ranges of lengths are intended to apply to all embodiments of the present invention described herein.

The back guards of the various embodiments of the present invention (as further discussed below) are intended to reach/extend to approximately the middle back area of the user without having to adjust (e.g., lower) the front portion of the article. With previous articles, the only way to raise the height of the back is to pull the back portion upward while pulling the front portion downward (i.e., toward the crotch of the user). However, when pulling the front portion downward, the user loses protection on his/her front torso areas. Thus, causing the same problems for the front torso area that occurred for the back torso area. In addition, it is often not possible to maintain the back portion in the elevated position because as the user shifted positions, the back portion falls back to its "normal" resting position about the small of the user's back.

Referring now to FIGS. 2A–E, an incontinence article 32 having a back guard 34 in a closed position (when not worn by a user), according to a first embodiment of the present invention is shown. As depicted, back guard 34 includes top portion 42, curved opposing side portions 44, and absorbent material 46. Moreover, as described above, article 32 includes an impermeable outer cover 38 (shown on front portion 36). Rear portion and front portion 36 are placed in a closed position using any means known in the art. For example, tabs 40 could be used to further couple front portion 36 to rear portion. Tabs 40 could use adhesive, hooks and loops, etc. Moreover, the quantity of tabs shown is not intended to be limiting. For example, article 32 could include four tabs. As indicated above, back guard 34 is intended to extend from rear portion to the middle back area of the user. As shown, when placed in a closed position without a user, back guard 34 extends well above front portion 36. In previous articles, the rear portion and front portion 36 were approximately parallel when placed in a closed position without a user. Thus, the only way to extend the previous article to the middle back area is to pull the front portion downward while pulling the back portion upward.

Referring to FIGS. 2B–D, elastic 48 could be used in conjunction with absorbent material 46. Elastic 48 is preferably positioned at any location(s) along a periphery of back guard 34. As shown in FIG. 2B, elastic 48 could be positioned along top portion 42. FIG. 2C shows that elastic 48 could be positioned along curved side portions 44. FIG. 2D demonstrates that elastic 48 could be positioned along the entire periphery of back guard 34 (i.e., along top portion 42 as well as curved side portions 44).

The various positions of elastic 48 on back guard 34 shown in FIGS. 2B–D are not intended to be exhaustive and it should be appreciated that other variations could exist. For example, elastic 48 could be positioned along top portion 42 and/or one curved side portion 44. Moreover, when elastic 48 is implemented, it is preferably positioned at a different location(s) (i.e., separately positioned/located) on back guard 34 than absorbent material 46. Specifically, elastic 48 is positioned along the periphery of back guard 34, while absorbent material is located centrally on back guard 34. Thus, back guard 34 could have two distinct regions: (1) an elastic region; and (2) an absorbent material region.

Figure 2E:
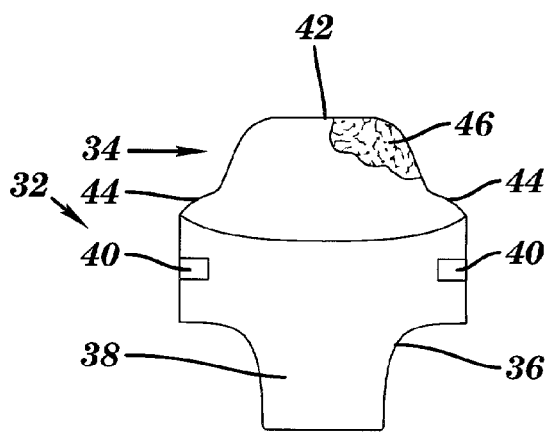
Figure 2E:
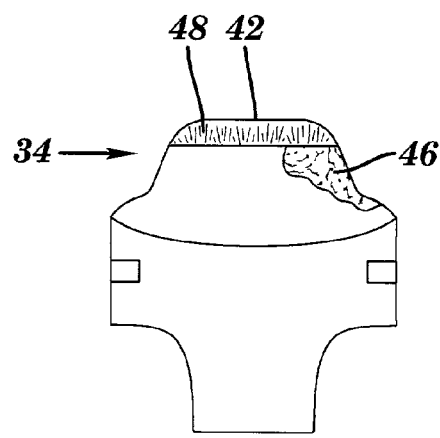
Figure 2E:
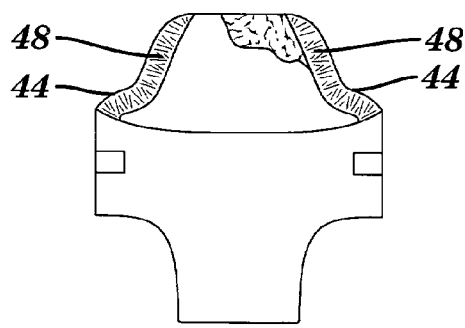
Figure 2E:
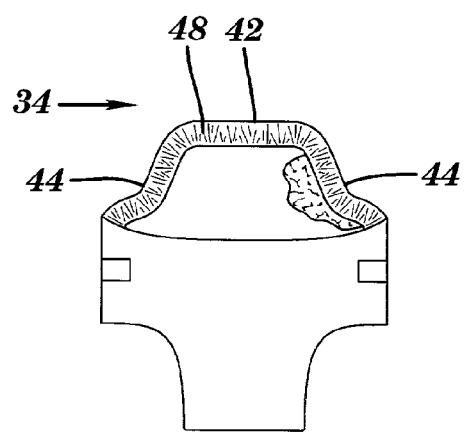
Figure 2E:
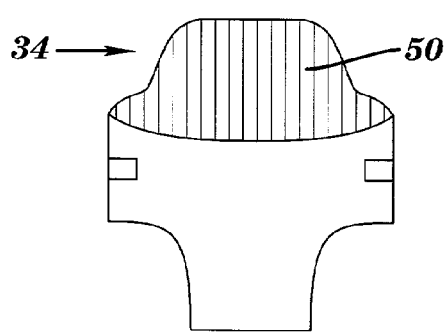

FIG. 2E shows that back guard 34 could also include rigid support structures or boning 50 to provide rigidity and support thereto. Structures 50 are preferably a series of stitches, or are plastic, wood, or metal rod-like articles inserted into back guard 34. Although shown as a series of vertically oriented articles, structures 50 could be implemented in any quantity (e.g., one), and could be horizontally oriented, diagonally oriented, or any combination thereof. Moreover, structures 50 are preferably used in conjunction with absorbent material, and optionally, with any configuration of elastic shown in FIGS. 2B–D.

FIGS. 3A–E show an incontinence article 52 having a back guard 54 in a closed position (when not worn by a user), according to a second embodiment of the present invention is shown. As depicted, back guard 54 includes top portion 62, linear opposing side portions 64, and absorbent material 66. As described above, article 52 includes an impermeable outer cover 58 (shown on front portion 56). Rear portion and front portion 56 are placed in a closed position using any means known in the art. For example, tabs 60 could be used to further couple front portion 56 to rear portion. Tabs 60 could use adhesive, hooks and loops, etc. Moreover, the quantity of tabs shown is not intended to be limiting. For example, article 52 could include four tabs. Back guard 54 is intended to extend from rear portion to the middle back area of the user. As shown, when placed in a closed position without a user, back guard 54 extends well above front portion 56. In previous articles, the rear portion and front portion 56 were approximately parallel when placed in a closed position without a user. Thus, the only way to extend the previous article to the middle back area is to pull the front portion downward while pulling the back portion upward.

Referring to FIGS. 3B–D, elastic 68 could be used in conjunction with absorbent material 66. Preferably, elastic 68 is positioned at any location(s) along a periphery of back guard 54. As shown in FIG. 3B, elastic 68 could be positioned along top portion 62. FIG. 3C shows that elastic 68 could be positioned along side portions 64. FIG. 3D demonstrates that elastic 68 could be positioned along the entire periphery of back guard 54 (i.e., along top portion 62 as well as side portions 64).

The various positions of elastic 68 on back guard 54 shown in FIGS. 3B–D are not intended to be exhaustive and it should be appreciated that other variations could exist. For example, elastic 68 could be positioned on top portion 62 and/or one side portion 64. Moreover, when elastic 68 is implemented, it is preferably positioned at a different location(s) (i.e., separately positioned) on back guard 54 than absorbent material 66. Specifically, elastic 68 is positioned along the periphery of back guard 54, while absorbent material is located centrally on back guard 54. Thus, back guard 54 could have two distinct regions: (1) an elastic region; and (2) an absorbent material region.

Figure 3E:
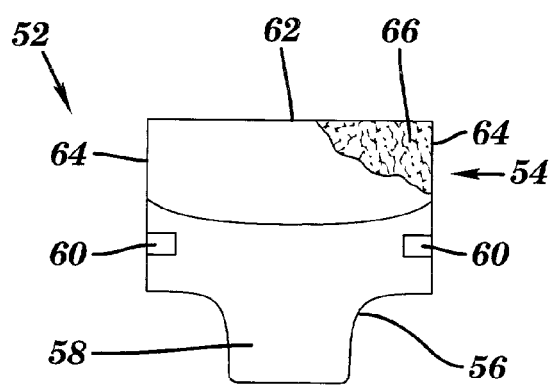
Figure 3E:
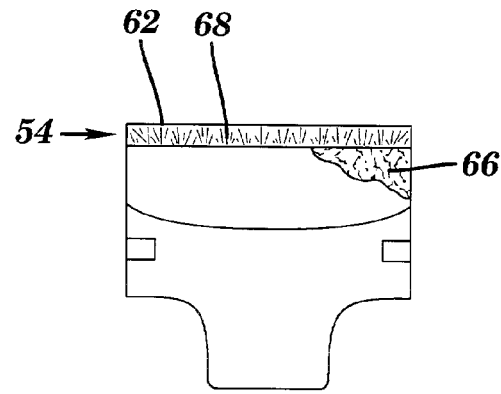
Figure 3E:
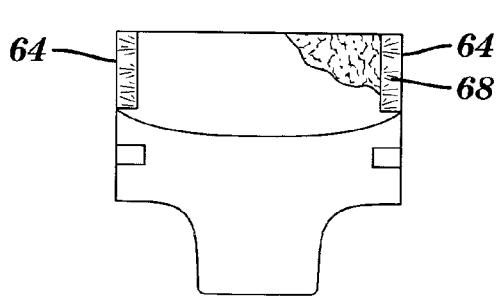
Figure 3E:
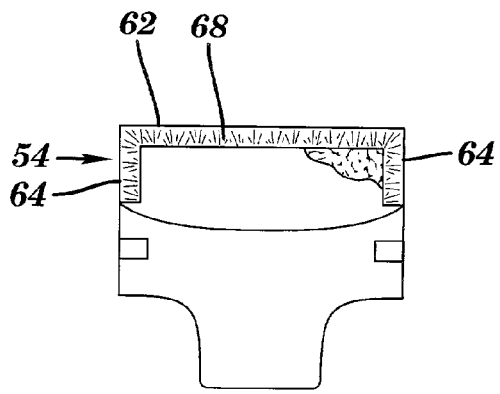
Figure 3E:
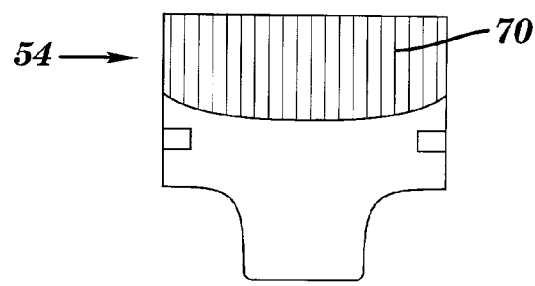

FIG. 3E shows that back guard 54 could also include rigid support structure or boning 70 to provide rigidity and support thereto. Structures 70 are preferably a series of stitches, or are plastic, wood, or metal rod-like articles inserted into back guard 54. Although shown as a series of vertically oriented articles, structures 70 could be implemented in any quantity (e.g., one), and could be horizontally oriented, diagonally oriented, or any combination thereof. Moreover, structures 70 are preferably used in conjunction with absorbent material, and optionally, with any configuration of elastic shown in FIGS. 3B–D.

Referring now to FIGS. 4A–E, an incontinence article 72 having a back guard 74 in a closed position (when not worn by a user), according to a third embodiment of the present invention is shown. As depicted, back guard 74 is curved and includes top portion 82, side portions 84, and absorbent material 86. As described above, article 72 includes an impermeable outer cover 80 (shown on front portion 78). Rear portion and front portion 78 are placed in a closed position using any means known in the art. For example, tabs 76 could be used to further couple front portion 78 to rear portion. Tabs 76 could use adhesive, hooks and loops, etc. Moreover, the quantity of tabs shown is not intended to be limiting. For example, article 72 could include four tabs. Back guard 74 is intended to extend from rear portion to the middle back area of the user. As shown, when placed in a closed position without a user, back guard 74 extends well above front portion 78. In previous articles, the rear portion and front portion 78 were approximately parallel when placed in a closed position without a user. Thus, the only way to extend the previous article to the middle back area is to pull the front portion downward while pulling the back portion upward.

Figure 4A:
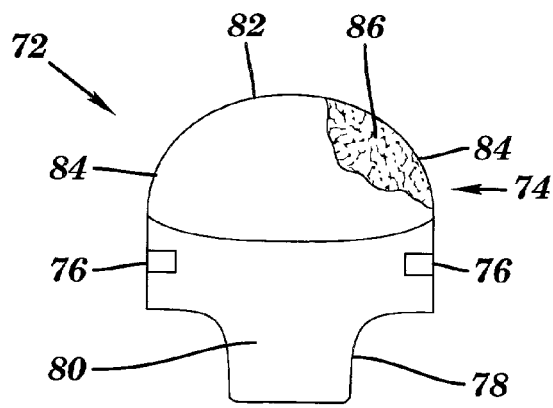
FIGS. 4A–E depict front views of an incontinence article having a back guard according to a third embodiment of the present invention.
Figure 4B:
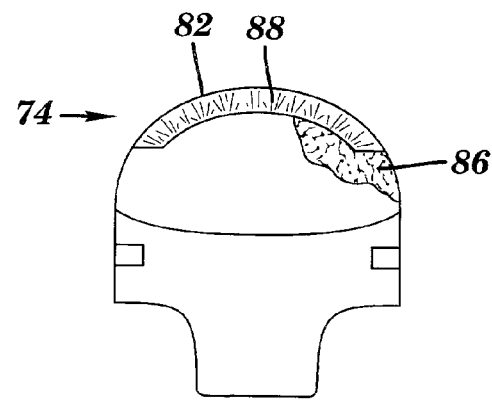
Figure 4C:
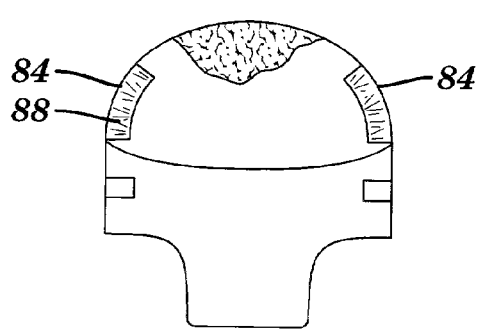
Figure 4D:
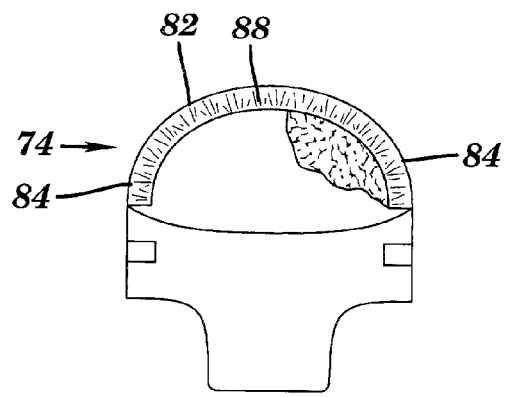

Referring to FIGS. 4B–D, elastic 88 could be used in conjunction with absorbent material 86. Preferably, elastic 88 is positioned at any location(s) along a periphery of back guard 74. As shown in FIG. 4B, elastic 88 could be positioned along top portion 82. FIG. 4C shows that elastic 88 could be positioned along side portions 84. FIG. 4D demonstrates that elastic 88 could be positioned along the entire periphery of back guard 74 (i.e., along top portion 82 as well as side portions 84).

The various positions of elastic 88 on back guard 74 shown in FIGS. 4B–D are not intended to be exhaustive and it should be appreciated that other variations could exist. For example, elastic 88 could be provided on top portion 82 and/or one side portion 84. Moreover, when elastic 88 is implemented, it is preferably positioned at a different location(s) (i.e., separately positioned) on back guard 74 than absorbent material 86. Specifically, elastic 88 is positioned along the periphery of back guard 74, while absorbent material is located centrally on back guard 74. Thus, back guard 74 could have two distinct regions: (1) an elastic region; and (2) an absorbent material region.

Figure 4E:
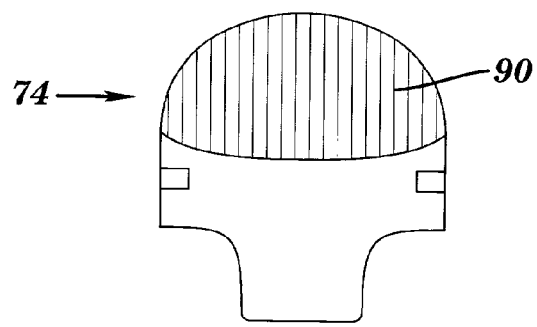

FIG. 4E shows that back guard 74 could also include rigid support structures or boning 90 to provide rigidity and support thereto. Structures 90 are preferably a series of stitches, or are plastic, wood, or metal rod-like articles inserted into back guard 74. Although shown as a series of vertically oriented articles, structures 90 could be implemented in any quantity (e.g., one), and could be horizontally oriented, diagonally oriented, or any combination thereof. Moreover, structures 90 are preferably used in conjunction with absorbent material, and optionally, with any configuration of elastic shown in FIGS. 4B–D.

Referring now to FIGS. 5A–I, an incontinence article 100 having a back guard 102 in a closed position (when not worn by a user), according to a fourth embodiment of the present invention is shown. As depicted, back guard 102 includes: (1) vertical extension 104 having top portion 108; (2) horizontal extensions 106 each having lower portion 110, upper portion 112, and side portion 114; and (3) absorbent material 116. Horizontal extensions 106 cause back guard 102 to have a width greater than a width of rear portion and front portion 118. As described above, article 100 includes an impermeable outer cover 120 (shown on front portion 118). Rear portion and front portion 118 are placed in a closed position using any means known in the art. For example, tabs 122 could be used to further couple front portion 118 to rear portion. Tabs 122 could use adhesive, hooks and loops, etc. Moreover, the quantity of tabs shown is not intended to be limiting. For example, article 100 could include four tabs. Back guard 102 is intended to extend from rear portion to the middle back area of a user. As shown, when placed in a closed position without a user, back guard 102 extends well above front portion 118. In previous articles, the rear portion and front portion 118 were approximately parallel when placed in a closed position without a user. Thus, the only way to extend the previous article to the middle back area is to pull the front portion downward while pulling the back portion upward.

Figure 5A:
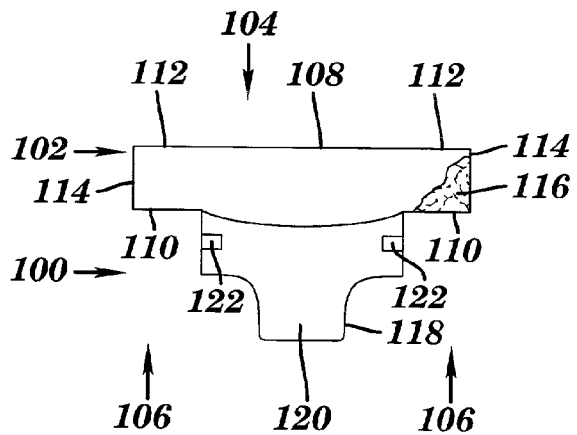
FIGS. 5A–I depict front views of an incontinence article having a back guard according to a fourth embodiment of the present invention.
Figure 5B:
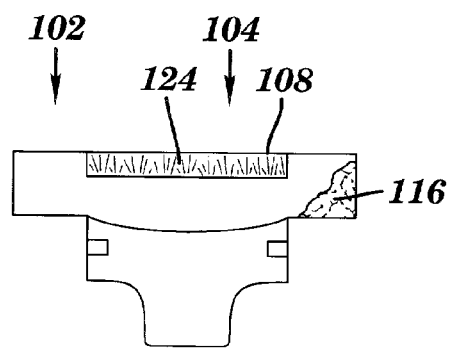
Figure 5C:
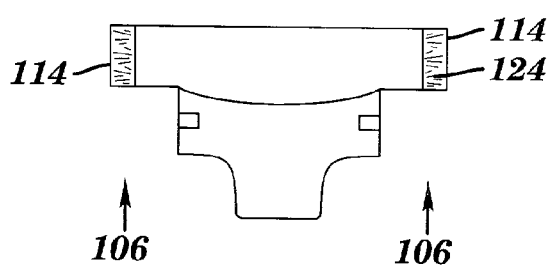
Figure 5D:
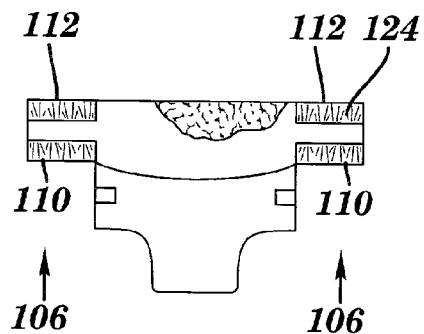
Figure 5E:
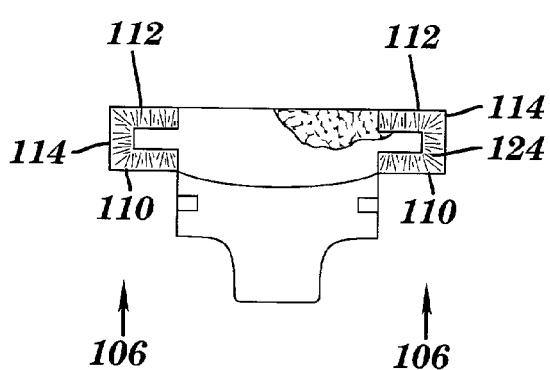
Figure 5F:
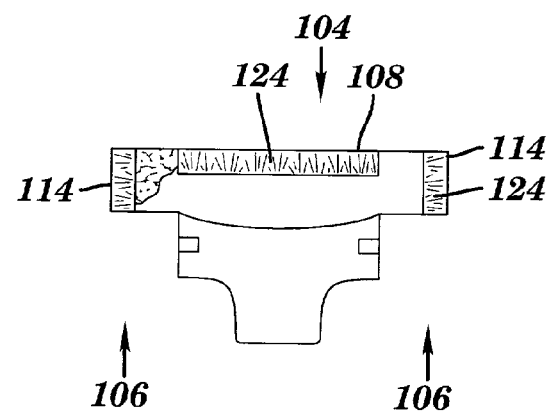
Figure 5G:
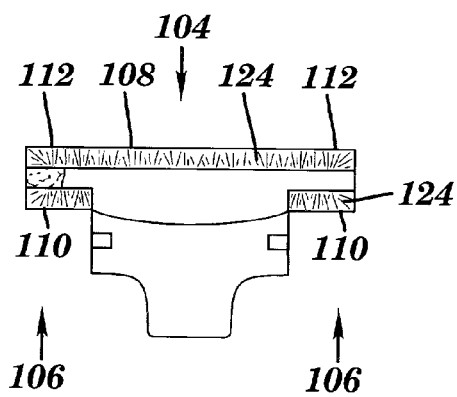
Figure 5H:
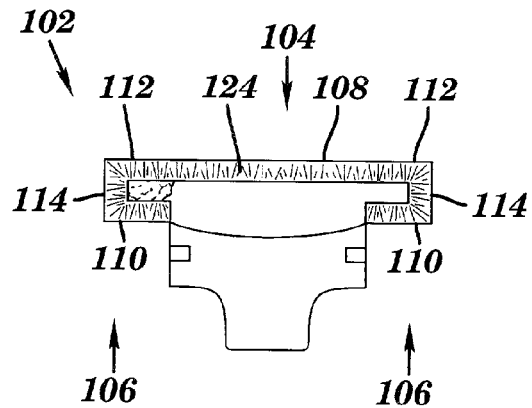

Referring to FIGS. 5B–H, elastic 124 could be used in conjunction with absorbent material 116. Preferably, elastic 124 is positioned at any location(s) along a periphery of back guard 102. As shown in FIG. 5B, elastic 124 could be positioned along top portion 108 of vertical extension 104. FIG. 5C shows that elastic 124 could be positioned along side portions 114 of horizontal extensions 106. FIG. 5D demonstrates that elastic 124 could be positioned along lower portions 110 and upper portions 112 of horizontal extensions 106. FIG. 5E demonstrates that elastic 124 could be positioned along the entire periphery of horizontal extensions 106 (i.e., lower portions 110, upper portions 112, and side portions 114). FIG. 5F demonstrates that elastic 124 could be positioned along side portions 114 of horizontal extensions 106 and top portion 108 of vertical extension 104. FIG. 5G demonstrates that elastic 124 could be positioned along top portion 108 of vertical extension 104 as well as lower portions 110 and upper portions 112 of horizontal extensions 106. FIG. 5H demonstrates that elastic 124 could be positioned along the entire periphery of the back guard 102 (i.e., along top portion 108 of vertical extension 104, and along lower portions 110, upper portions 112, and side portions 114 of horizontal extensions 106).

The examples shown in FIGS. 5B–H are not intended to be exhaustive and it should be appreciated that other combinations of elastic positioning could exist. For example, elastic 124 could be provided in lower portions 110 and side portions 114, but not in upper portions 112. Moreover, when elastic 124 is implemented, it is preferably positioned at a different location(s) (i.e., separately position/located) on back guard 102 than absorbent material 116. Specifically, elastic 124 is positioned along the periphery of back guard 102, while absorbent material is located centrally on back guard 102. Thus, back guard 102 could have two distinct regions: (1) an elastic region; and (2) an absorbent material region.

Figure 5I:
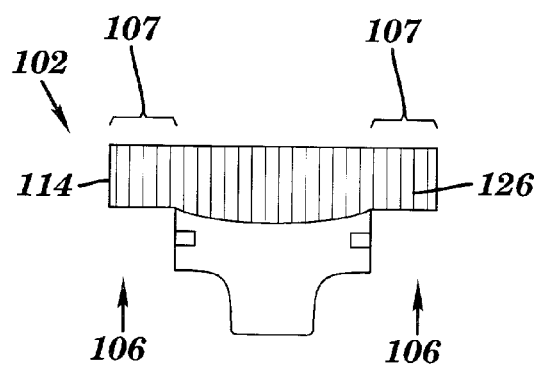

FIG. 5I shows that back guard 102 could also include rigid support structures or boning 126 to provide rigidity and support thereto. Structures 126 are preferably a series of stitches, or are plastic, wood, or metal rod-like articles inserted into back guard 102. Although shown as a series of vertically oriented articles, structures 126 could be implemented in any quantity (e.g., one), and could be horizontally oriented, diagonally oriented, or any combination thereof. Moreover, structures 126 are preferably used in conjunction with absorbent material, and optionally, with any configuration of elastic shown in FIGS. 5B–H. As further shown in FIG. 5I, horizontal extensions 106 each have a length 107 that is at least 1.0 inches. Preferably, length 107 is approximately 1.0 to 10.0 inches, or any value or range of values therebetween. It should be understood that these values for length 107 of horizontal extensions 106 are intended to apply to any of FIGS. 5A–I.

Figure 6G:
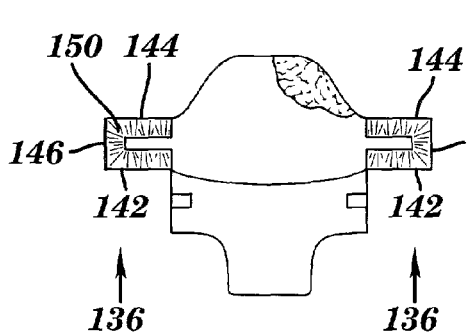
FIGS. 6A–O depict front views of an incontinence article having a back guard according to a fifth embodiment of the present invention.
Figure 6H:
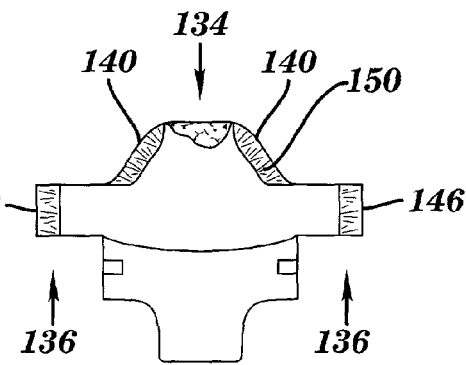
Figure 6I:
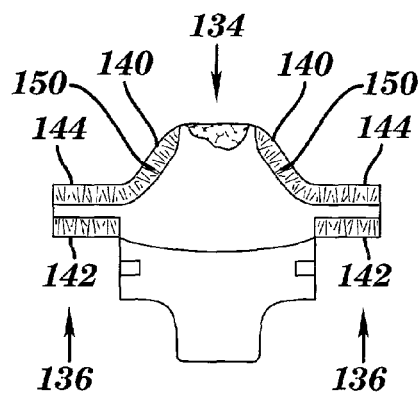
Figure 6J:
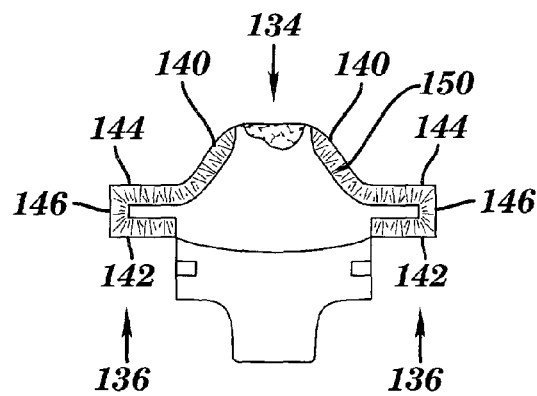
Figure 6K:
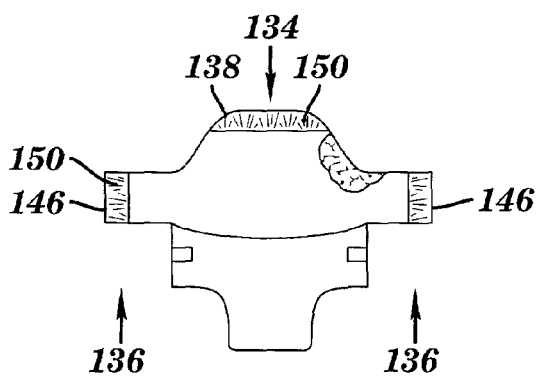
Figure 6L:
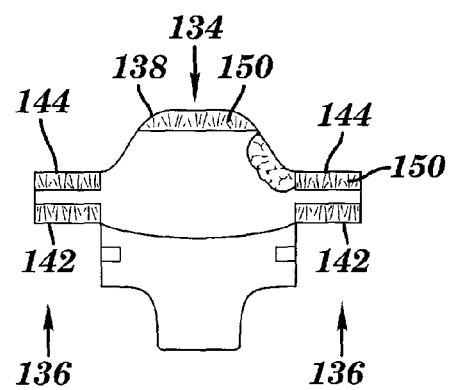
Figure 6M:
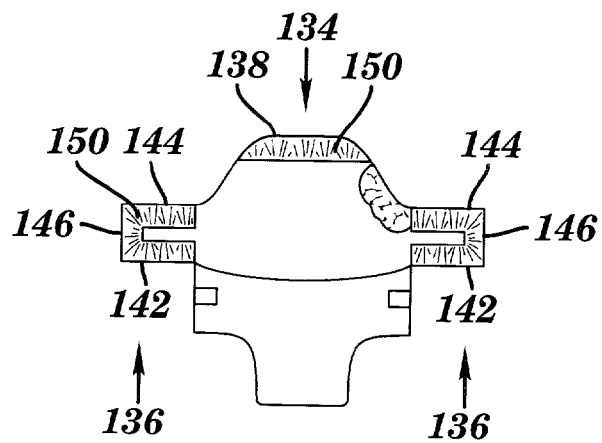
Figure 6N:
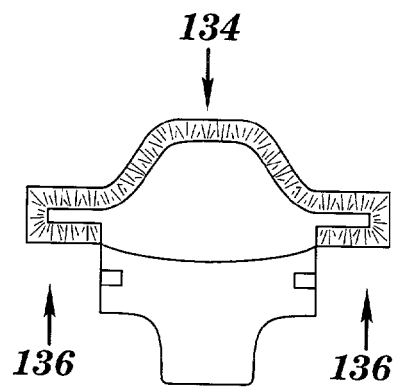
Figure 6O:
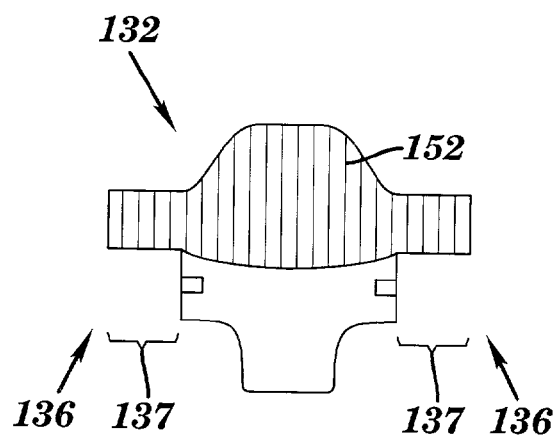

Referring now to FIGS. 6A–O, an incontinence article 130 having a back guard 132 in a closed position (when not worn by a user), according to a fifth embodiment of the present invention is shown. As depicted, back guard 132 includes: (1) vertical extension 134 having top portion 138, and angular side portions 140; (2) horizontal extensions 136 each having lower portion 142, upper portion 144, and side portion 146; and (3) absorbent material 148. Horizontal extensions 136 cause back guard 132 to have a width greater than a width of rear portion and front portion 151. As described above, article 130 includes an impermeable outer cover 152 (shown on front portion 151). Rear portion and front portion 151 are placed in a closed position using any means known in the art. For example, tabs 148 could be used to further couple front portion 151 to rear portion. Tabs 148 could use adhesive, hooks and loops, etc. Moreover, the quantity of tabs shown is not intended to be limiting. For example, article 130 could include four tabs. Back guard 132 is intended to extend from rear portion to the middle back area of a user. As shown, when placed in a closed position without a user, back guard 132 extends well above front portion 151. In previous articles, the rear portion and front portion 151 were approximately parallel when placed in a closed position without a user. Thus, the only way to extend the previous article to the middle back area was to pull the front portion downward while pulling the back portion upward.

Referring to FIGS. 6B–N, elastic 150 could be used in conjunction with absorbent material 148. Preferably, elastic 150 is positioned at any location(s) along a periphery of back guard 132. As shown in FIG. 6B, elastic 150 could be positioned along top portion 138 of vertical extension 134. FIG. 6C shows that elastic 150 could be positioned along angular side portions 140 of vertical extension 134. FIG. 6D demonstrates that elastic 150 could be positioned along the entire periphery (i.e., top portion 138 and angular side portions 140) of vertical extension 134. FIG. 6E demonstrates that elastic 150 could be positioned along side portions 146 of horizontal extensions 136. FIG. 6F demonstrates that elastic 150 could be positioned along lower portions 142 and upper portions 144 of horizontal extensions 136. FIG. 6G demonstrates that elastic 150 could be positioned along the entire periphery (i.e., lower portions 142, upper portions 144, and side portions 146) of horizontal extensions 136. FIG. 6H demonstrates that elastic 150 could be positioned along angular side portions 140 of vertical extension 134, and side portions 146 of horizontal extensions 136. FIG. 6I demonstrates that elastic 150 could be positioned along angular side portions 140 of vertical extension 134, and lower portions 142 and upper portions 144 of horizontal extensions 136. FIG. 6J demonstrates that elastic 150 could be positioned along the entire periphery (i.e., lower portions 142, upper portions 144, and side portions 146) of horizontal extensions 136, and angular side portions 140 of vertical extension 134. FIG. 6K demonstrates that elastic 150 could be positioned along top portion 138 of vertical extension 134, and side portions 146 of horizontal extensions 136. FIG. 6L demonstrates that elastic 150 could be positioned along top portion 138 of vertical extension 134, and lower portions 142 and upper portions 144 of horizontal extensions 136. FIG. 6M demonstrates that elastic 150 could be positioned along top portion 138 of vertical extension 134, and the entire periphery (i.e., lower portions 142, upper portions 144, and side portions 146 of horizontal extensions 136). FIG. 6N demonstrates that elastic 150 could be positioned along the entire periphery (i.e., vertical extension 134 and horizontal extensions 136) of the back guard.

The examples shown in FIGS. 6B–N are not intended to be exhaustive and it should be appreciated that other combinations of elastic positioning could exist. For example, elastic 150 could be provided in lower portions 142 and side portions 146, but not in upper portions 112. Moreover, when elastic 150 is implemented, it is preferably positioned at a different location(s) (i.e., separately position/located) on back guard 132 than absorbent material 148. Specifically, elastic 150 is positioned along the periphery of back guard 132, while absorbent material is located centrally on back guard 132. Thus, back guard 132 could have two distinct regions: (1) an elastic region; and (2) an absorbent material region.

FIG. 6O shows that back guard 132 could also include rigid support structures or boning 152 to provide rigidity and support thereto. Structures 152 are preferably a series of stitches, or are plastic, wood, or metal rod-like articles inserted into back guard 132. Although shown as a series of vertically oriented articles, structures 152 could be implemented in any quantity (e.g., one), and could be horizontally oriented, diagonally oriented, or any combination thereof. Moreover, structures 152 are preferably used in conjunction with absorbent material, and optionally, with any configuration of elastic shown in FIGS. 6B–N. As further shown in FIG. 6O, horizontal extensions 136 each have a length 137 that is at least 1.0 inches. Preferably, length 137 is approximately 1.0 to 10.0 inches, or any value or range of values therebetween. It should be understood that these values for length 137 of horizontal extensions 136 are intended to apply to any of FIGS. 6A–O.

Figure 7A:
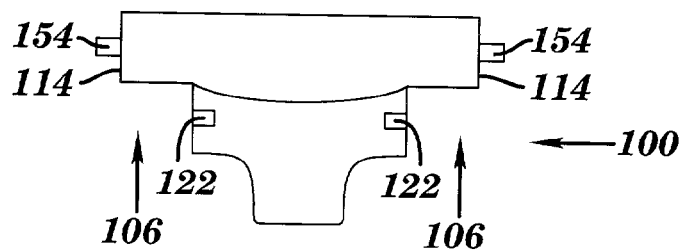
FIGS. 7A–B depict front views the incontinence articles of FIGS. 5A–I in an open position and a first closed position, respectively.
Figure 7B:
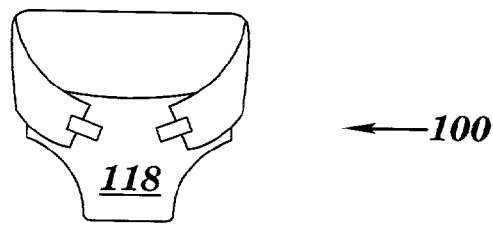
Figure 7C:
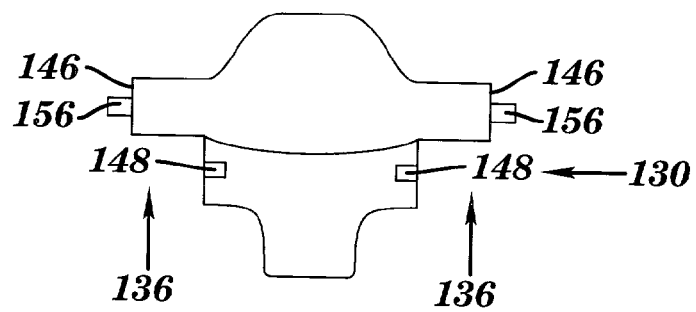
FIGS. 7C–D depict front views the incontinence articles of FIGS. 6A–O in an open position and a first closed position, respectively.
Figure 7D:
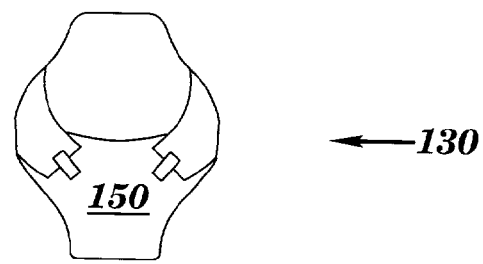

Referring now to FIGS. 7A–B, an example of article 100 of FIGS. 5A–I in a partially closed position and a fully closed position is shown (when not worn by a user). As depicted, article 100 includes tabs 154 on an outer surface of side portions 114 of horizontal extensions 106. FIG. 7B, shows that article 100 can be closed by diagonally coupling horizontal extensions 106 to front portion 118 (in addition to using tabs 122 to couple front portion 118 to rear portion). Specifically, horizontal extensions 106 fold inward and downward so that tabs 154 can couple to front portion 118. FIGS. 7C–D show a similar closing convention for article 130 of FIGS. 6A–O. Specifically, horizontal extensions 136 include tabs 156 on an outer surface of side portions 146. Horizontal extensions 136 fold inward and downward to diagonally couple to front portion 150. It should be understood that tabs 122 and 148 depicted in FIGS. 7A–D are optional. Specifically, tabs 122 and 148 could be used in conjunction with tabs 154 and 156, or could be substituted for by tabs 154 and 156.

Figure 8A:
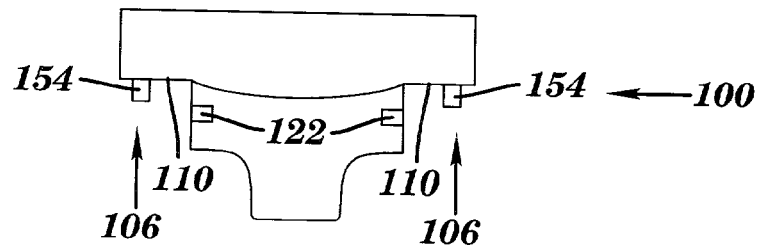
FIGS. 8A–B depict front views the incontinence articles of FIGS. 5A–I in an open position and a second closed position, respectively.
Figure 8B:
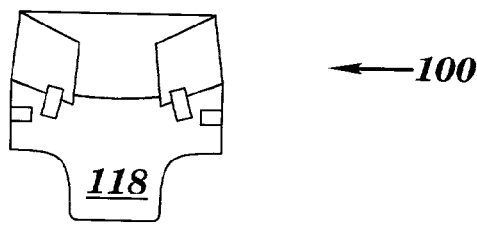
Figure 8C:
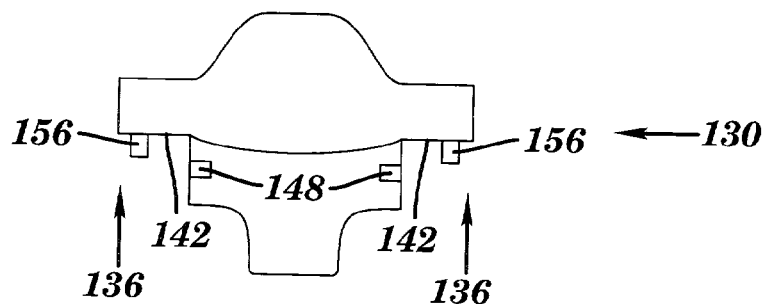
FIGS. 8C–D depict front views the incontinence articles of FIGS. 6A–O in an open position and a second closed position, respectively.
Figure 8D:
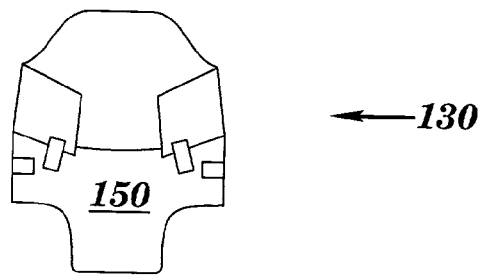

FIGS. 8A–B show an alternative closing convention for article 100. Specifically, tabs 154 are provided on an outer surface lower portions 110 of horizontal extensions 106. Horizontal extensions 106 fold inward and then laterally couple to front portion 118, as shown in FIG. 8B. FIGS. 8C–D shows a similar closing convention for article 130. As show, tabs 156 are attached to an outer surface of lower portions 142 of horizontal extensions 136. Horizontal extensions 136 fold inward for lateral coupling to front portion 150. Similar to FIGS. 7A–7D, it should be understood that tabs 122 and 148 depicted in FIGS. 8A–D are optional. Specifically, tabs 122 and 148 could be used in conjunction with tabs 154 and 156, or could by substituted for by tabs 154 and 156.

It should be understood that the closing conventions shown in FIGS. 7A–D and 8A–D are intended to be illustrative only and other variations could exist. For example, additional tabs could be provided, and/or the tabs could be located on other portions of the articles.

Figure 9:
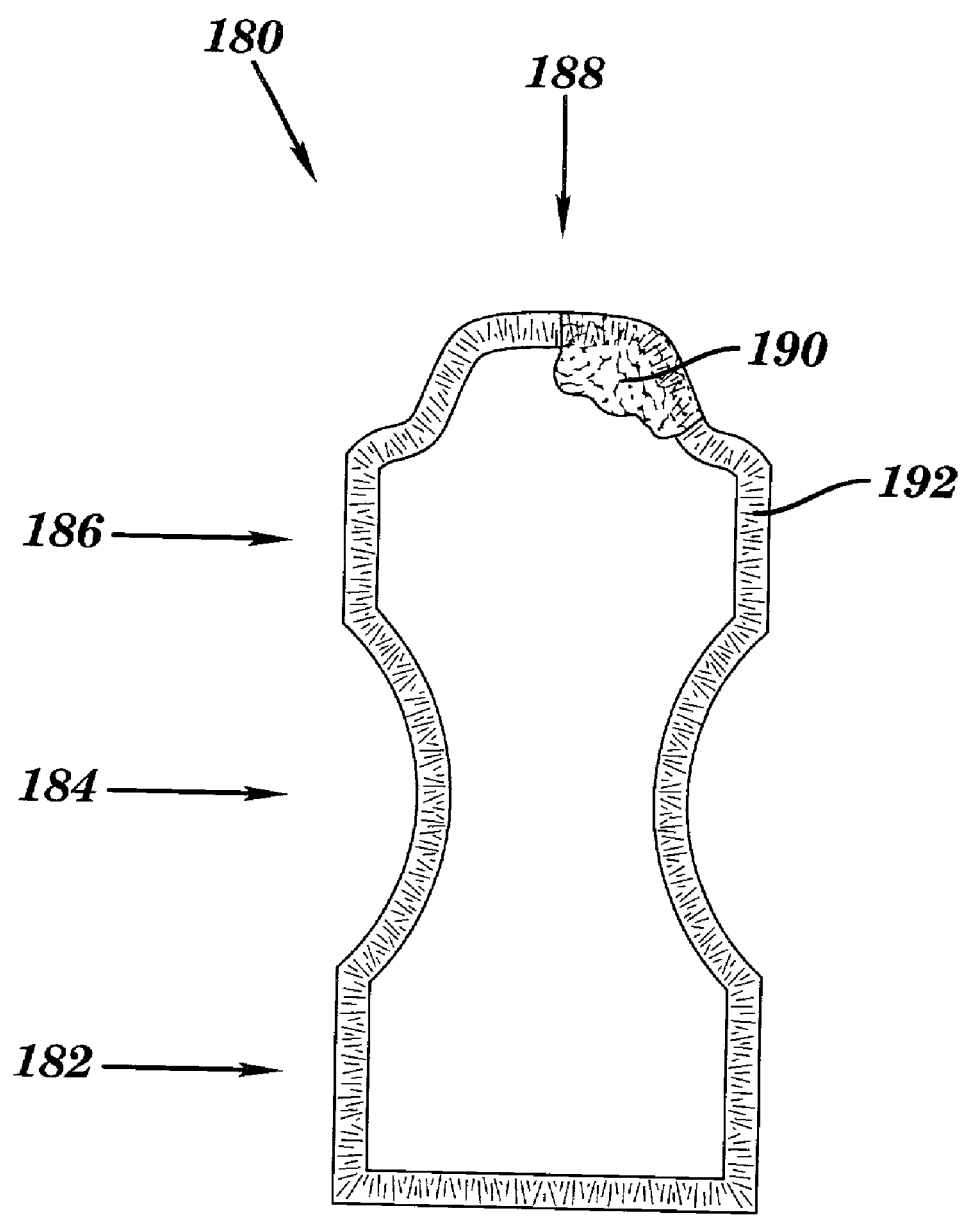
FIG. 9 depicts a plan view of an incontinence article having a back guard according to sixth embodiment of the present invention.

Referring now to FIG. 9, an article 180 according to a sixth embodiment of the present invention is shown. As depicted, article 180 includes front portion 182, crotch portion 184, rear portion 186, and back guard 188 extending from rear portion 186. Similar to the previous embodiments, back guard 188 extends to the middle back area of the user without having to adjust the positioning of front portion 182. However, under this embodiment of the present invention, elastic 192 is used in the same region(s) as absorbent material 190. Conversely, under the previous embodiments shown in FIGS. 1–8, the absorbent material is used in a different region than the elastic (i.e., the two are separately positioned) to create two distinct regions. However, the embodiment depicted in FIG. 9, shows that absorbent material 190 and elastic 192 can co-exist in the same region (i.e. are commonly positioned). It should be understood that article 180 can include any of the back guards and corresponding elastic arrangements shown and described in conjunction with FIGS. 1–8. Elastic 192 has been shown about the entire periphery of back guard 188 for illustrative purposes only.

Figure 10:
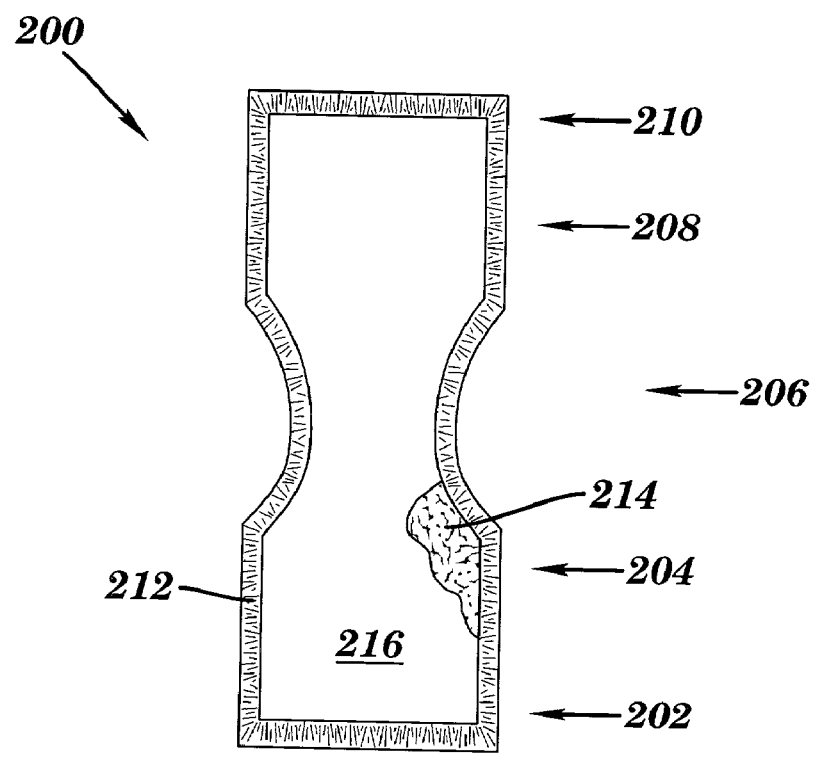
FIG. 10 depicts a front view of an incontinence article having a front guard and a back guard according to a seventh embodiment of the present invention.

Referring now to FIG. 10, an article 200 according to a seventh embodiment of the present invention is shown. In particular, article 200 includes front guard 202 extending from front portion 204, crotch portion 206, back guard 210 extending from rear portion 208, elastic 212, and absorbent material 214. Article 200 preferably has components and construction similar to article 10 of FIG. 1. Specifically, article 200 is preferably a multilayered composite structure having a liquid permeable body-side layer 216, an impermeable outer cover (not shown in FIG. 10), and an absorbent material 214 positioned therebetween. Moreover, front guard 202 and back guard 210 preferably have the same possible lengths/range of lengths as back guard 18 described above in conjunction with FIG. 1. A purpose of having both a front guard as well as a back guard is to protect both the front and back torso areas of a user.

Figure 11:
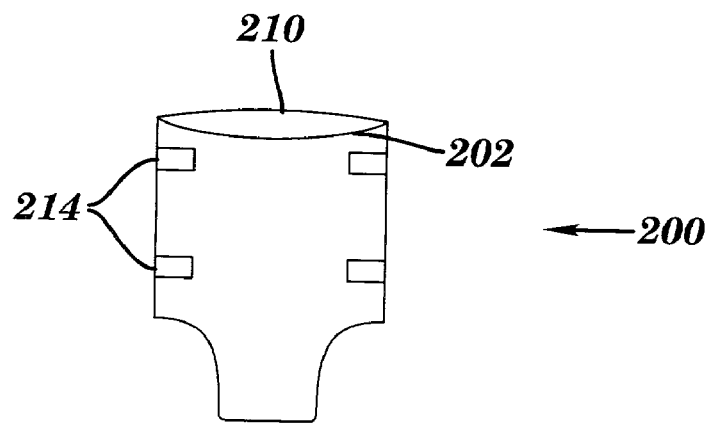
FIG. 11 depicts a front view of the incontinence article of FIG. 10 in a closed position.

FIG. 11 shows article 200 in a closed positioned (when not worn by a user). As can be seen, article 200 is constructed so that back guard 210 will extend to a middle back area of a user, while front guard 202 will extend to a middle chest area of the user. It should be appreciated that front guard 202 and back guard 210 resemble the back guard 62 shown in FIGS. 3A–D for clarity purposes only. For example, front guard 202 and back guard 210 could resemble any back guard shown in the other figures. Moreover, although elastic 212 is shown as being positioned about a periphery of the entire article 200, it should be appreciated that any configuration of elastic could be implemented (as shown and described above in conjunction with FIGS. 1–9). For example, elastic 212 could be eliminated from front guard 202 and/or back guard 210.

As further shown in FIG. 11, article 200 includes tabs 214 for securing front portion 204 and rear portion 208 in a closed position. This is one possible embodiment and is not intended to be limiting. For example, article 200 could include a different quantity of tabs. In addition, front guard 202 and/or back guard 210 could be provided with horizontal and vertical extensions (similar to articles 100 and 130 of FIGS. 5A–I and 6A–O, respectively).

Figure 12:
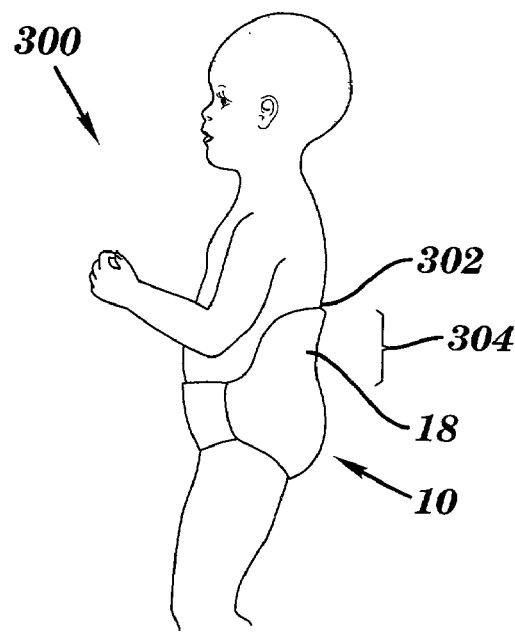
FIG. 12 depicts an incontinence article having a back guard when worn by a user.

FIG. 12 shows article 10 of FIG. 1 as worn by a user 300. It should be understood that article 10 is depicted in FIG. 12 for illustration purposes only and all other embodiments shown and described herein could be worn by user 300. For example, FIG. 12 could depict user 300 wearing article 100 of FIGS. 5A–I. As shown, back guard 18 extends to a middle back area 302 of user 300. Since various users will be different sizes, the length of back guard 18 will vary. Accordingly, back guard 18 can have any length or range of lengths 304 as described above in conjunction with FIG. 1.

Figure 13:
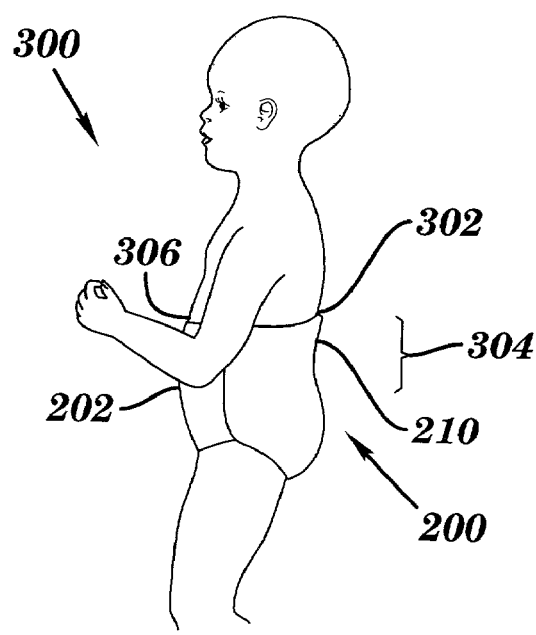
FIG. 13 depicts an incontinence article having a front guard and a back guard when worn by a user.

FIG. 13 shows article 200 of FIGS. 10 and 11 as worn by user 300. As depicted front guard 202 and back guard 210 extend to a middle chest area 306 and a middle back area 302, respectively, of user 300. As indicated above, since various users will be different sizes, length 304 of front guard 202 and back guard 210 will vary. Accordingly, front guard 202 and back guard 210 can have any length 304 described above in conjunction with FIG. 1. In addition, front guard 202 and back guard 210 of article 200 can have any of the configurations of the back guards of FIGS. 1–6A–I. For example, front guard 202 and back guard 210 could have vertical and horizontal extensions.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. An incontinence article, comprising:
    a front portion positioned adjacent to a front pelvic area and extending from a waist area to a crotch area when the article is worn by a user;
    a rear portion joined to the front portion, the rear portion being positioned adjacent to a rear pelvic area and extending from the waist area to the crotch area when the article is worn by the user, further wherein the front portion and the rear portion extend vertically to an article waistline, being substantially a same level vertically when worn by the user; and
    a back guard extending vertically from the rear portion, further wherein the back guard fully extends above the article waistline when the article is worn by the user, wherein the back guard comprises an absorbent material and a separately positioned elastic.

2. The continence article of claim 1, wherein the elastic is positioned at a predetermined location about a periphery of the back guard, and wherein the absorbent material is positioned centrally on the back guard.

3. The incontinence article of claim 1, wherein the back guard further comprises opposing side portions and a top portion.

4. The incontinence article of claim 3, wherein the side portions are curved.

5. The incontinence article of claim 3, wherein the side portions are linear.

6. The incontinence article of claim 1, wherein the back guard is curved.

7. The incontinence article of claim 1, wherein the back guard has a length of approximately 1.0 to 10.0 inches, and wherein the back guard extends to a middle back area when the article is worn by the user.

8. An incontinence article, comprising:
    a front portion positioned adjacent to a front pelvic area and extending from a waist area to a crotch area when the article is worn by a user;
    a rear portion joined to the front portion, the rear portion being positioned adjacent to a rear pelvic area and extending from the waist area to the crotch area when the article is worn by the user, further wherein the front portion and the rear portion extend vertically to an article waistline, being substantially a same level vertically when worn by the user; and
    a back guard extending vertically from the rear portion, further wherein the back guard fully extends above the article waistline when the article is worn by the user, wherein the back guard, having a T-shaped outline, comprises a vertical extension and opposing horizontal extensions that extend laterally outward from outer edges of the vertical extension.

9. The incontinence article of claim 8, wherein the back guard further comprises an absorbent material and separately positioned elastic.

10. The incontinence article of claim 9, wherein the elastic is positioned at a predetermined location about a periphery of the back guard.

11. The incontinence article of claim 9, wherein the elastic is positioned about a periphery of the horizontal extensions.

12. The incontinence article of claim 9, wherein the elastic is positioned about a periphery of the vertical extension.

13. The incontinence article of claim 9, wherein the elastic is positioned about a periphery of the horizontal extensions and a periphery of the vertical extensions.

14. The incontinence article of claim 8, wherein the back guard has a width greater than a width of the rear portion.

15. The incontinence article of claim 8, wherein the vertical extension includes opposing side portions and a top portion.

16. The incontinence article of claim 8, wherein the horizontal extensions diagonally couple to the front portion.

17. The incontinence article of claim 8, wherein the horizontal extensions laterally couple to the front portion.

18. The incontinence article of claim 8, wherein the vertical extension extends to a middle back area when the article is worn by the user.

19. The incontinence article of claim 8, wherein the vertical extension has a length of approximately 1.0 to 10.0 inches.

20. The incontinence article of claim 8, wherein each horizontal extension has a length of approximately 1.0 to 10.0 inches.

21. An incontinence article, comprising:
a front portion positioned adjacent to a front pelvic area and extending from a waist area to a crotch area when the article is worn by a user;
a front guard extending vertically from the front portion to a middle chest area of the user;
a rear portion joined to the front portion, the rear portion being positioned adjacent to a rear pelvic area and extending from the waist area to the crotch area when the article is worn by the user, further wherein the front portion and the rear portion extend vertically to an article waistline, being substantially a same level vertically when worn by the user;
a back guard extending vertically from the rear portion to a middle back area when the article is worn by the user, further wherein the back guard fully extends above the article waistline when the article is worn by the user; and
wherein the front and rear portions each comprise an absorbent material, further wherein the back guard having elastic positioned only about a periphery thereof.

22. The incontinence article of claim 21, wherein the front guard and the back guard each further comprise a centrally positioned absorbent material.

23. The incontinence article of claim 22, wherein the front guard and the rear guard each further comprise elastic positioned about a periphery thereof.

24. The incontinence article of claim 21, wherein the front guard and the back guard each have a length of approximately 1.0 to 10.0 inches.

25. An incontinence article, comprising:
a front portion positioned adjacent to a front pelvic area and extending from a waist area to a crotch area when the article is worn by a user;
a rear portion joined to the front portion, the rear portion being positioned adjacent to a rear pelvic area and extending from the waist area to the crotch area when the article is worn by the user, further wherein the front portion and the rear portion extend vertically to an article waistline, being substantially a same level vertically when worn by the user; and
a back guard extending vertically from the rear portion, further wherein the back guard fully extends above the article waistline when the article is worn by the user, wherein the back guard comprises an absorbent material and elastic.

26. The incontinence article of claim 25, wherein the back guard extends to a middle back area when the article is worn by the user.

27. The incontinence article of claim 25, wherein the elastic and absorbent material are commonly positioned.

28. The incontinence article of claim 25, wherein the elastic and absorbent material are separately positioned.

* * * * *